US 6,734,312 B2

(12) United States Patent
Reynolds et al.

(10) Patent No.: US 6,734,312 B2
(45) Date of Patent: May 11, 2004

(54) PROCESS FOR PREPARING A COMPOUND CONTAINING A HETEROAROMATIC GROUP WITH ONE OR MORE ETHER SUBSTITUENTS

(75) Inventors: John R. Reynolds, Gainesville, FL (US); Bert Groenendaal, Sinaai (BE); Kyukwan Zong, Spartanburg, SC (US); Luis Madrigal, Gainesville, FL (US)

(73) Assignee: Agfa-Gevaert, Mortsel (BE)

( * ) Notice: Subject to any disclaimer, the term of this patent is extended or adjusted under 35 U.S.C. 154(b) by 0 days.

(21) Appl. No.: 10/325,424

(22) Filed: Dec. 20, 2002

(65) Prior Publication Data

US 2003/0162958 A1 Aug. 28, 2003

Related U.S. Application Data

(60) Provisional application No. 60/344,076, filed on Dec. 28, 2001, and provisional application No. 60/384,025, filed on May 29, 2002.

(51) Int. Cl.$^7$ ..................... C07D 495/02; C07D 487/02
(52) U.S. Cl. .......................... 549/50; 548/453
(58) Field of Search .............................. 549/50; 548/453

(56) References Cited

U.S. PATENT DOCUMENTS

| | | | |
|---|---|---|---|
| 5,111,327 A | | 5/1992 | Blohm et al. |
| 6,359,149 B1 | * | 3/2002 | Tan et al. ................... 549/50 |
| 6,369,239 B2 | * | 4/2002 | Rauchschwalbe et al. .... 549/50 |
| 6,512,120 B1 | * | 1/2003 | Mishra et al. ............... 546/113 |
| 6,528,662 B2 | * | 3/2003 | Jonas ........................ 549/50 |

FOREIGN PATENT DOCUMENTS

| | | |
|---|---|---|
| DE | 100 29 075 A1 | 12/2001 |
| JP | 2001 163879 | 6/2001 |

OTHER PUBLICATIONS

Dallacker et al.; *Chem Ber.*, 108, 569–575 (1975).
Gogte et al.; *Tetrahedron*, 23, 2437–2441 (1967).
Groenendaal et al.; *Advanced Materials*, 12 (7), 481–494 (2000).
Halfpenny et al., *J. Chem. Soc. Perkin Trans.* 1, 2595–2603 (2001).
Holzer et al.; *Monatshefte für Chemie*, 125, 1287–1291 (1994).
Hughes, *Organic Preparations and Procedures Int.*, 28 (2), 127–164 (1996).
Merz et al.; *Synthesis*, 795–800 (Jul. 1995).
Murashima et al.; *Tetrahedron Letters*, 37 (18), 3133–3136 (1996).
Paquette et al. (Eds.), *Organic Reactions*, vol. 42, 335–343, 350–354, 385–386, 473–490, 636–656, John Wiley & Sons, New York (1992).
Pei et al.; *Polymer*, 35 (7), 1347–1351 (1994).
Welsh et al.; *Advanced Materials*, 11 (16), 1379–1382 (1999).
Zong et al.; *J. Org. Chem.*, 66, 6873–6882 (2001).
International Search Report, PCT/EP02/13153 (Mar. 31, 2003).
Dallacker et al.; *Chem. Ber.*, 108, 576–581 (1975).
Skotheim et al. (eds.); *Handbook of Conducting Polymer*, 2$^{nd}$ ed., New York, N.Y., Marcel Dekker (1998).

* cited by examiner

*Primary Examiner*—Deborah C. Lambkin
(74) *Attorney, Agent, or Firm*—Leydig, Voit & Mayer, Ltd.

(57) ABSTRACT

A process for preparing a heteroaromatic compound having a heteroaromatic nucleus substituted with one or more ether groups comprising the step of: condensing at least one hydroxy-group of a compound having said heteroaromatic nucleus, said at least one hydroxy group (—OH) being substituted at α- or β-positions with respect to a heteroatom of said heteroaromatic nucleus, with an alcohol containing one or more primary or secondary alcohol groups, optionally substituted with nitro, amide, ester, halogen, cyano or (hetero)aromatic groups, using the redox couple of a triaryl- or trialkylphosphine and an azodioxo-compound at a temperature between –40° C. and 160° C.

10 Claims, No Drawings

PROCESS FOR PREPARING A COMPOUND CONTAINING A HETEROAROMATIC GROUP WITH ONE OR MORE ETHER SUBSTITUENTS

The application claims the benefit of U.S. Provisional Application No. 60/344,076 filed Dec. 28, 2001 and of U.S. Provisional Application No. 60/384,025 filed May 29, 2002, which are both incorporated by reference.

FIELD OF THE INVENTION

The present invention relates to a process for preparing a heteroaromatic compound having a heteroaromatic nucleus substituted with one or more ether groups.

BACKGROUND OF THE INVENTION.

Polythiophenes and polypyrroles have been studied extensively due to their interesting electrical and/or optical properties (see Handbook of Conducting Polymers, Eds. Skotheim, T. A.; Elsenbaumer, R. L.; Reynolds, J. R., Marcel Dekker, New York, 1998, 2nd edition). Within these classes of electroconductive polymers, poly(3,4-alkylenedioxythiophenes) and poly(3,4-alkylenedioxypyrroles) have particularly useful electrical and/or optical properties. Poly(3,4-ethylenedioxythiophene) [PEDOT] in association with the polyanion poly(styrene sulfonic acid) [PSS] is one of the most commercially successful conductive polymers in the world. It is being used in a wide variety of applications as described by L. Groenendaal et al. in 2000 in Advanced Materials, volume 12, pages 481–494.

Two routes for preparing the monomers from which poly(3,4-alkylenedioxythiophenes) and poly(3,4-alkylenedioxypyrroles) are prepared, 3,4-alkylenedioxythiophenes, such as 2,3-dihydro-thieno [3,4-b][1,4]dioxine [also known as 3,4-ethylenedioxythiophene (EDOT)], and 3,4-alkylenedioxypyrroles have been disclosed: via a double Williamsson synthesis [see Pei et al. in 1994 in Polymer, volume 35, pages 1347–1351, for thiophene derivatives, and J. R. Reynolds et al. in 2001 in Journal of Organic Chemistry, volume 66, pages 6873–6882, and A. Merz et al. in 1995 in Synthesis, pages 795–800, for pyrrole derivatives], via the alkylation procedure reported by Halfpenny et al. in 2001 in Journal Chemistry Society, Perkins Transaction I, pages 2595–2603 who modified the alkylation procedure reported by Dallacker and Mues in 1975 in Chemische Berichte, volume 108, page 576 by using 1,2-bromoethane instead of bromochloromethane, and via transetherification of 3,4-dimethoxythiophene (see Reynolds et al in 1999 in Advanced Materials, volume 11, pages 1379–1382).

The double Williamson route and the alkylation procedure suffers from the disadvantages that it mostly uses $\alpha,\omega$-dichloro- or $\alpha,\omega$-dibromo-alkanes, which with short chain alkanes such as ethane or propane are extremely toxic, for the ring closure and that substituted derivatives (at the 2-position of the dioxine ring) are, if obtainable, only obtainable in low to very low yields.

The transetherification route has the disadvantages of involving the difficult and expensive synthesis of 3,4-dimethoxy-derivatives (not commercially available) and the low yields for reactions involving secondary alcohol groups. Furthermore, it is not possible to use this reaction for the preparation of pyrrole derivatives.

There is therefore a need for an alternative process for preparing 3,4-alkylenedioxythiophenes and 3,4-alkylenedioxypyrroles avoiding the above-mentioned problems.

OBJECTS OF THE INVENTION

It is therefore an aspect of the present invention to provide a process for preparing 3,4-alkylenedioxythiophenes and 3,4-alkylenedioxypyrroles in high yields, avoiding expensive and toxic intermediates.

Further aspects and advantages of the invention will become apparent from the description hereinafter.

SUMMARY OF THE INVENTION

It has been surprisingly found that the Mitsunobu reaction can be used to prepare a heteroaromatic compound having a heteroaromatic nucleus substituted with one or more ether groups at $\alpha$- or $\beta$-positions with respect to a heteroatom of the heteroaromatic nucleus, whereas the Mitsunobu reaction is typically used for condensing alcohols with an acidic compound (H—Nu) such as oxygen nucleophiles for example carboxylic acids and phenols; nitrogen nucleophiles for example imides, hydroxamates, and heterocycles; sulfur nucleophiles for example thiols and thioamides; and carbon nucleophiles for example $\beta$-ketoesters.

Aspects of the present invention have been realized by a process for preparing a heteroaromatic compound having a heteroaromatic nucleus substituted with one or more ether groups comprising the step of: condensing at least one hydroxy-group of a compound having the heteroaromatic nucleus, the at least one hydroxy group (—OH) being substituted at $\alpha$- or $\beta$-positions with respect to a heteroatom of the heteroaromatic nucleus, with an alcohol containing one or more primary or secondary alcohol groups, optionally substituted with nitro, amide, ester, halogen, cyano or (hetero)aromatic groups using the redox couple of a triaryl- or trialkylphosphine and an azodioxo-compound at a temperature between –40° C. and 160° C. The heteroaromatic nucleus for the above-disclosed heteroaromatic compound and the above-disclosed compound are identical.

Further advantages and embodiments of the present invention will become apparent from the following description.

DETAILED DESCRIPTION OF THE INVENTION

Definitions

By a heteroaromatic nucleus is meant a heteroaromatic ring comprising carbon and non-carbon atoms with no substituents other than hydrogen atoms.

Substituted at the _$\alpha$-position relative to a heteroatom of a heteroaromatic nucleus means substituted at a carbon atom directly adjacent to a heteroatom of a heteroaromatic nucleus. There are two $\alpha$-positions relative to a heteroatom of a heteroaromatic nucleus either side of the heteroatom.

$\beta$-position relative to a heteroatom of a heteroaromatic nucleus means substituted at a carbon atom directly adjacent to the α-position relative to a heteroatom in a heteroaromatic nucleus. There are two β-positions relative to a heteroatom of a heteroaromatic nucleus on the non-heteroatom side of each of the two α-positions relative to a heteroatom in the heteroaromatic nucleus.

The Mitsunobu reaction is the condensation reaction of alcohols with an acidic compound (H—Nu) using the redox couple of a triaryl- or trialkylphosphine and an azodioxo-compound in which the triaryl- or trialkylphosphine is oxidised to the corresponding phosphine oxide and the azodioxo-compound is reduced to the corresponding hydrazine, as described in Organic Reactions 1992, Vol. 42, 335–656 (Chapter 2 entitled "The Mitsunobu reaction" by D. L. Hughes), and Organic Preparations and Procedures International, 1996, Vol. 28(2), 127–164 ("Progress in the Mitsunobu Reaction. A Review" by D. L. Hughes).

The term alkyl means all variants possible for each number of carbon atoms in the alkyl group i.e. for three carbon atoms: n-propyl and isopropyl; for four carbon atoms: n-butyl, isobutyl and t-butyl; for five carbon atoms: n-pentyl, 1,1-dimethyl-propyl, 2,2-dimethylpropyl and 2-methyl-butyl etc.

A chiral compound is a compound containing a chiral centre. A chiral centre is an atom, e.g. a carbon atom, that is attached to four different groups. A compound containing a chiral centre is not superimposable upon its mirror image and will exhibit chirality, chirality being the handedness of an asymmetric molecule. Such compounds, if isolated in a pure state, will generally exhibit rotation of polarized light detectable with a polarimeter.

Bu represents an n-butyl group.

Ph represents a phenyl group.

Process for Preparing a Compound Containing a Heteroaromatic Nucleus Substituted With one or More Ether Groups According to the present invention, a process for preparing a heteroaromatic compound having a heteroaromatic nucleus substituted with one or more ether groups comprising the step of: condensing at least one hydroxy-group of a compound having said heteroaromatic nucleus, said at least one hydroxy group (—OH) being substituted at α- or β-positions with respect to a heteroatom of said heteroaromatic nucleus, with an alcohol containing one or more primary or secondary alcohol groups, optionally substituted with nitro, amide, ester, halogen, cyano or (hetero)aromatic groups, using the redox couple of a triaryl- or trialkylphosphine and an azodioxo-compound at a temperature between −40° C. and 160° C.

According to a first aspect of the process, according to the present invention, the compound has at least two hydroxy groups substituted at α- or β-positions with respect to a heteroatom of said heteroaromatic nucleus.

According to a second aspect of the process, according to the present invention, the condensation is carried out at a temperature between 20° C. and 80° C.

According to a third aspect of the process, according to the present invention, the heteroaromatic nucleus is selected from the group consisting of pyridine, thiazole, isoxazole, imidazole, pyrazole, 1,2,3-triazole, furan, thiophene, pyrrole, selenophene, pyrazine, pyridazine and pyrimidine.

According to a fourth aspect of the process, according to the present invention, the heteroaromatic nucleus of said compound is further substituted with a nitro, amide, ester, cyano, acyl, acyloxy, carbonate, alkyl, aryl, carbocyclic or heterocyclic group.

According to a fifth aspect of the process, according to the present invention, the heteroaromatic nucleus is annulated to a carbocyclic or a heterocyclic ring system.

According to a sixth aspect of the process, according to the present invention, the annulated heteroaromatic nucleus is selected from the group consisting of indole, isoindole, thianaphthene, benzimidazole, benzofuran, quinoline, isoquinoline, cinnoline and quinoxaline.

According to a seventh aspect of the process, according to the present invention, the alcohol is an optionally substituted diol represented by formula (I):

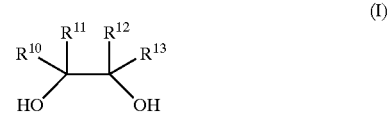

wherein $R^{10}$, $R^{11}$, $R^{12}$ and $R^{13}$ independently represent hydrogen or alkyl, alkoxy or acyl groups optionally substituted with nitro, amide, ester, halogen, cyano or (hetero)aromatic groups.

According to an eighth aspect of the process, according to the present invention, the alcohol is an optionally substituted diol represented by formula (II):

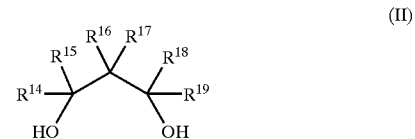

where $R^{14}$, $R^{15}$, $R^{16}$, $R^{17}$, $R^{18}$ and $R^{19}$ independently represent hydrogen or alkyl, alkoxy or acyl groups optionally substituted with nitro, amide, ester, halogen, cyano or (hetero)aromatic groups. Optionally substituted 1,4-diols and 1,5-diols can also be used.

According to an ninth aspect of the process, according to the present invention, the alcohol is selected from the group consisting of 1,2-ethanediol (ethylene glycol), 2,3-butanediol, 1,2-butanediol, 1,3-propanediol, 2,2-dimethyl-1,3-propanediol, 2,2-diethyl-1,3-propanediol, 2,2-di-n-propyl-1,3-propanediol, 2,2-di-n-butyl-1,3-propanediol, 2,2-bis(bromomethyl)-1,3-propanediol, 3,3-bis(hydroxymethyl)-pentane, 2,2-bis(hydroxymethyl)-propane, 1,4-butanediol, 5,5-bis(hydroxymethyl)-nonane, 3,3-bis(hydroxymethyl)-heptane, 2,4-pentanediol and 1,2-dodecanediol.

Examples of suitable alcohols are methanol, ethanol and higher homologues optionally substituted with nitro, amide, ester, cyano or (hetero)aromatic groups, polyols, optionally substituted with nitro, amide, ester, halogen, cyano or (hetero)aromatic groups, such as glycol and other diols, glycerol and other triols, and derivatives with more than three alcohol groups.

According to a tenth aspect of the process, according to the present invention, the heteroaromatic compound having a heteroaromatic nucleus substituted with one or more ether groups is represented by the formula (III):

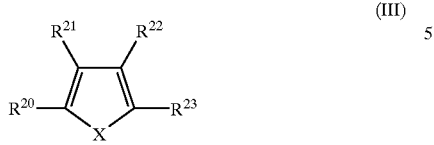

where $R^{20}$, $R^{21}$, $R^{22}$ and $R^{23}$ independently represent unsaturated or saturated substituents such as alkyl or alkoxy groups optionally substituted with nitro, amine, amide, ester, cyano or (hetero)aromatic groups or $R^{20}$ together with $R^{21}$ or $R^{21}$ together with $R^{22}$, or $R^{22}$ together with $R^{23}$ represent the atoms necessary to complete an aromatic, heteroaromatic, heterocyclic or carbocyclic ring system with the proviso that at least one of $R^{20}$, $R^{21}$, $R^{22}$ and $R^{23}$ is an optionally substituted alkoxy group, and X is S, O or N—$R^{24}$, where $R^{24}$ is an optionally substituted acyl or alkyl group e.g. a benzoyl or benzyl group.

According to an eleventh aspect of the process, according to the present invention, the heteroaromatic compound having a heteroaromatic nucleus substituted with one or more ether groups is represented by formula (IV):

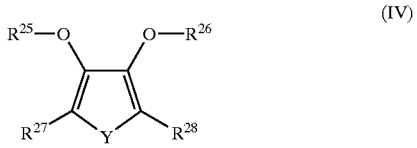

wherein $R^{25}$ and $R^{26}$ independently represent optionally substituted alkyl, alkoxy, carboxy or cycloalkyl substituents or $R^{25}$ and $R^{26}$ jointly represent the atoms necessary to form a heterocyclic ring, $R^{27}$ and $R^{28}$ represent $CO_2R^{29}$ substituents with $R_{29}$ being an alkyl group e.g. methyl, ethyl, propyl or butyl and Y being S or N—$R^{30}$ where $R^{30}$ is an optionally substituted acyl or alkyl group e.g. a benzoyl or benzyl group.

According to a twelfth aspect of the process, according to the present invention, the heteroaromatic compound having a heteroaromatic nucleus substituted with one or more ether groups is a 3,4-ethylenedioxythiophene or a 3,4-ethylenedioxypyrrole represented by formula (V):

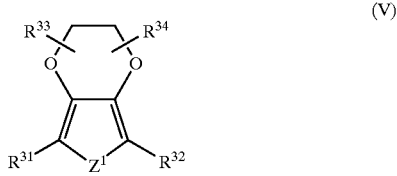

wherein $R^{31}$ and $R^{32}$ independently represent optionally substituted alkyl, alkoxy, carboxy or cycloalkyl substituents, $R^{33}$ and $R^{34}$ independently represent unsaturated or saturated substituents such as alkyl or alkoxy groups optionally substituted with nitro, amide, ester, cyano or (hetero) aromatic groups, and $Z^1$ is S or N—$R^{35}$ where $R^{35}$ is an optionally substituted acyl or alkyl group e.g. a benzoyl or benzyl group.

According to a thirteenth aspect of the process, according to the present invention, the heteroaromatic compound having a heteroaromatic nucleus substituted with one or more ether groups is a 3,4-propylenedioxythiophene or a 3,4-propylenedioxypyrrole represented by formula (VI):

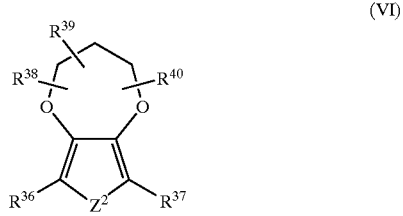

wherein $R^{36}$ and $R^{37}$ independently represent optionally substituted alkyl, alkoxy, carboxy or cycloalkyl substituents, $R^{38}$, $R^{39}$ and $R^{40}$ independently represent unsaturated or saturated substituents such as alkyl or alkoxy groups optionally substituted with nitro, amide, ester, cyano or (hetero) aromatic groups, and $Z^2$ is S or N—$R^{41}$ where $R^{41}$ is an optionally substituted acyl or alkyl group e.g. a benzoyl or a benzyl group.

Larger ring systems (e.g. butylenedioxy systems) can also be prepared via this route.

Polyols react with heteroaromatic nuclei substituted with at least two hydroxy (—OH) substituents at α- or β-positions with respect to a heteroatom of the heteroaromatic nucleus to form alkylenedioxy-bridges between adjacent or non-adjacent carbon atoms of the heteroaromatic nucleus.

According to a fourteenth aspect of the process, according to the present invention, the heteroaromatic compound having a heteroaromatic, e.g. thiophene or pyrrole, nucleus substituted with one or more ether groups is chiral. This will depend upon the substitution pattern.

While it was found that the Mitsunobu reaction was somewhat sensitive to the degree of steric congestion of the alcohol employed (in fact tertiary alcohols do not react), the route is generally applicable to the synthesis of a host of dioxane ring functionalized thiophene.

The theoretical minimum molar ratio of azodicarboxylate to phosphine is 1. A ratio of up to 1.5 can be used, a molar ratio of 1.2 being found to be generally beneficial.

According to a fifteenth aspect of the process, according to the present invention, the molar ratio of azodioxocompound to triaryl- or trialkylphosphine is 1.0 to 1.2.

The theoretical minimum ratio of azodioxo-compound or phosphine per hydroxy group is 1.0, with 1.25 being overkill.

According to a sixteenth aspect of the process, according to the present invention, the molar ratio of azodioxocompound per hydroxy group is 1 to 1.2.

In a typical procedure, diethyl azodicarboxylate (2.4 equiv.) was dropwise added to a solution of 3,4-dihydroxythiophene-2,5-dicarboxylic acid diethyl ester (1.0 equiv.), diol (1.0 equiv.), and tributylphosphine (2.0 equiv.) in dry THF under argon at 25° C. The reaction mixture was stirred for 1 h and stirred at reflux for 4–24 h. The reaction was cooled and THF was removed by a rotary evaporator. The residue was diluted with ether and stood for crystallization of tributylphosphine oxide for 12 h. Tributylphosphine oxide was filtered off and the filtrate was concentrated. Purification of the residue by chromatography on silica gel using hexane/ethyl acetate as an eluent afforded the desired product.

Suitable solvents for use in the process, according to the present invention, include tetrahydrofuran, dioxane, dichloromethane, chloroform, diethyl ether, dimethylformamide, toluene, benzene and hexamethylphosphoramide.

Azodioxo-compounds

According to a seventeenth aspect of the process, according to the present invention, the azodioxo-compound is selected from the group consisting of diethyl azodicarboxylate, diisopropyl azodicarboxylate, 1,1'-(azodicarbonyl)dipiperidine and N,N,N',N'-tetramethylazodicarboxamide, as well as diazo derivatives mentioned in the following literature references: Organic Reactions 1992, Vol. 42, 335–656 (Chapter 2 entitled "The Mitsunobu reaction" by D. L. Hughes), and Organic Preparations and Procedures International, 1996, Vol. 28(2), 127–164 ("Progress in the Mitsunobu Reaction. A Review" by D. L. Hughes) herein incorporated by reference.

Suitable azodicarboxylate ingredients, according to the present invention, are:

| Azodicarboxylate type | |
|---|---|
| ADC01 | = diethyl azodicarboxylate |
| ADC02 | = di-isopropyl azodicarboxylate |
| ADC03 | = 1,1'-(azodicarbonyl)dipiperidine |
| ADC04 | = N,N,N',N'-tetramethylazodicarboxamide |

Triaryl- or Trialkyl-phosphines

According to an eighteenth aspect of the process, according to the present invention, the triaryl- or trialkyl-phosphine is selected from the group consisting of triphenylphosphine, tri-n-butylphosphine, tris(dimethylamino)phosphine, (4-dimethylamino)-diphenylphosphine, diphenyl(2-pyridyl)phosphine as well as phosphine derivatives mentioned in the following references:

Organic Reactions 1992, Vol. 42, 335–656 (Chapter 2 entitled "The Mitsunobu reaction" by D. L. Hughes), and Organic Preparations and Procedures International, 1996, Vol. 28(2), 127–164 ("Progress in the Mitsunobu Reaction. A Review" by D. L. Hughes) herein incorporated by reference.

Suitable phosphine ingredients, according to the present invention, are:

| Phosphine type | | |
|---|---|---|
| PH01 | = | tri-n-butylphosphine |
| PH02 | = | triphenylphosphine |

The invention is illustrated hereinafter by way of comparative and invention examples. The percentages and ratios given in these examples are by weight unless otherwise indicated.

COMPARATIVE EXAMPLE 1

Synthesis of 2,3-Dimethyl-2,3-dihydro-thieno[3,4-b][1,4]dioxine via the Transetherification Reaction A solution of 3,4-dimethoxythiophene (7.2 g, 50 mmol), meso-2,3-butanediol (5.4 g, 60 mmol), and p-toluenesulphonic acid (0.2 g) in toluene (100 ml) was heated at 100° C. under a continuous argon flow for 24 h. The reaction mixture was then poured into methylene chloride (200 mL) and the organic phase washed with a 1M aqueous solution of sodium hydrogen carbonate and brine, dried with anhydrous magnesium sulphate and concentrated. This resulted in a mixture of cis and trans product that could be separated by column chromatography, yielding pure cis (2.8 g, 16%) and trans (1.83 g, 11%) 2,3-dimethyl-2,3-dihydro-thieno[3,4-b][1,4]dioxine.

COMPARATIVE EXAMPLE 2

Synthesis of 2,3-Dimethyl-2,3-dihydro-thieno[3,4-b][1,4]dioxine-5,7-dicarboxylic Acid Diethyl Ester via the Double Williamson Reaction Potassium carbonate (3.19 g, 23.1 mmol) was added in portions to a solution of 3,4-dihydroxythiophene-2,5-dicarboxylate acid diethyl ester (2.0 g, 7.7 mmol) in N,N-dimethylacetamide (50 ml), blanketed by argon. The mixture was then heated for 1 h at 45° C. after which a solution of 2,3-dibromobutane (1.67 g, 7.7 mmol) in N,N-dimethylacetamide (10 ml) was added dropwise. The mixture was then heated for a further 24 h at 95° C. after which it was cooled to 25° C. A small sample was neutralized and analyzed with thin layer chromatography. This analysis indicated that the reaction gave a very poor yield of 2,3-dimethyl-2,3-dihydro-thieno[3,4-b][1,4]dioxine-5,7-dicarboxylic acid diethyl ester (<5%).

COMPARATIVE EXAMPLE 3

Synthesis of 3,3-diethyl-3,4-dihydro-2H-thieno[3,4-b][1,4]dioxepine via the transetherification reaction 3,4-Dimethoxythiophene (5.0 g, 34.7 mmol), 2,2-diethyl-1,3-propanediol (36.4 mmol), toluenesulfonic acid (0.2 g), and dry toluene (200 mL) were placed in a 500 mL round bottom flask equipped with a soxhlet extractor that contained a molecular sieve (4A)-filled extraction thimble. The solution was refluxed for 12 h under argon atmosphere, then cooled to 25° C. The solvent was removed under reduced pressure, the mixture diluted with 250 mL diethyl ether, extracted with 5% ammonium hydroxide (200 mL), and the extracted with water (2×200 mL). The organic layer was dried over anhydrous magnesium sulphate and the ether distilled off under reduced pressure, leaving an oil. This oil was further purified using column chromatography (silica and hexanes/ethyl acetate, 90/10) to yield 3,3-diethyl-3,4-dihydro-2H-thieno[3,4-b][1,4]dioxepine as a colourless oil in 68% yield.

COMPARATIVE EXAMPLE 4

Synthesis of 6-benzyl-2,3-dihydro-6H-[1,4]dioxino [2,3-c]pyrrole-5,7-dicarboxylic Acid Dimethyl Ester via the Williamson Route A mixture of dimethyl N-benzyl-3,4-dihydroxypyrrole-2,5-dicarboxylate (0.1 mol), 1,2-dibromoethane (0.1 mol), and potassium carbonate (0.5 mol) in dry DMF was stirred for 12 h under argon at 105–110° C. After cooling to 25° C., the reaction mixture was poured onto ice-water. The crude product was collected by suction filtration and purified by recrystallization in methanol yielding 6-benzyl-2,3-dihydro-6H-[1,4]dioxino[2,3-c]pyrrole-5,7-dicarboxylic acid dimethyl ester as colourless crystals in 55–65% yield.

INVENTION EXAMPLE 1

Synthesis of 2,3-Dihydro-thieno[3,4-b][1,4]dioxine-5,7-dicarboxylic Acid Diethyl Ester via the Mitsunobu Reaction ADC01 (2.9 g, 16.9 mmol) was slowly added to a solution of 3,4-dihydroxythiophene-2,5-dicarboxylic acid diethyl ester (2.0 g, 7.7 mmol), ethylene glycol (0.5 g, 8.5 mmol), and PH02 (4.4 g, 16.9 mmol) in dry tetrahydrofuran (150 ml) at 25° C. At 25° C. the reaction was slow and 2,3-dihydro-thieno[3,4-b][1,4]dioxine-5,7-dicarboxylic acid diethyl ester was obtained in 30–40% yield after 3 days. It was found that the reaction could be highly facilitated by heating. Stirring of the reaction mixture for 3 h followed by refluxing for 9 h (66° C.) gave yields of 90%. After refluxing the reaction mixture was allowed to cool to 25° C. and was concentrated by rotary evaporator to remove the THF. The residue was then diluted with diethyl ether and allowed to stand overnight to enable the triphenylphosphine oxide to precipitate out. The triphenylphosphine oxide was then removed by filtration and the residue purified by chromatography on silica gel (eluant: ethyl acetate/ hexane=2/1) to give 2.0 g of 2,3-dihydro-thieno[3,4-b][1,4]dioxine-5,7-dicarboxylic acid diethyl ester as white crystals (90% yield) as characterized by $^1$H NMR, $^{13}$C NMR, HRMS, and elemental analysis.

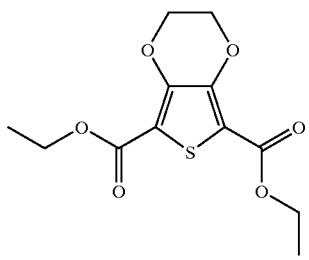

This diethyl ester could be hydrolyzed and decarboxylated following the procedures described by Kumar et al. in 1998 in Chemistry of Materials, volume 10, pages 896–902, to yield pure 3,4-ethylenedioxythiophene in excellent yield.

INVENTION EXAMPLE 2

Synthesis of 2,3-dihydro-thieno[3,4-b][1,4]dioxine-5,7-dicarboxylic Acid Diethyl Ester via the Mitsunobu Reaction ADC01 (2.9 g, 16.9 mmol) was slowly added to a solution of 3,4-dihydroxythiophene-2,5-dicarboxylic acid diethyl ester (2.0 g, 7.7 mmol), ethylene glycol (0.5 g, 8.5 mmol), and PHOL (3.4 g, 16.9 mmol) in dry tetrahydrofuran (150 ml) at 25° C. The reaction mixture was stirred for 3 h and then refluxed for 9 h. The reaction mixture was allowed to cool to 25° C. and concentrated by rotary evaporator to remove the THF. The residue was diluted with diethyl ether and allowed to stand overnight to enable the tributylphosphine oxide to precipitate out. The tributylphosphine oxide was then removed by filtration and the residue purified by chromatography on silica gel (eluant: ethyl acetate/ hexane=2/1) to give 2.1 g of 2,3-dihydro-thieno[3,4-b][1,4]dioxine-5,7-dicarboxylic acid diethyl ester as white crystals (95% yield) as fully characterized by $^1$H NMR, $^{13}$C NMR, HRMS, and elemental analysis.

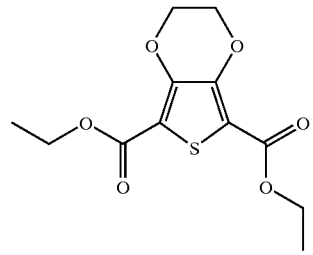

This diethyl ester could be hydrolyzed and decarboxylated following the procedures described by Kumar et al. in 1998 in Chemistry of Materials, volume 10, pages 896–902, to yield pure 3,4-ethylenedioxythiophene in excellent yield.

INVENTION EXAMPLE 3

Synthesis of 2,3-Dimethyl-2,3-dihydro-thieno[3,4-b][1,4]dioxine-5,7-dicarboxylic Acid Diethyl Ester via the Mitsunobu Reaction ADC01 (2.9 g, 16.9 mmol) was slowly added to a solution of 3,4-dihydroxythiophene-2,5-dicarboxylate acid diethyl ester (2.0 g, 7.7 mmol), meso-2,3-butanediol (0.77 g, 8.5 mmol), and PHOL (3.4 g, 16.9 mmol) in dry tetrahydrofuran (150 ml) at 25° C. The reaction mixture was stirred for 3 h and then refluxed for 21 h. The reaction mixture was allowed to cool to 25° C. and concentrated by rotary evaporator to remove the tetrahydrofuran. The residue was diluted with diethyl ether allowed to stand overnight to enable the tributylphosphine oxide to precipitate out. The tributylphosphine oxide was then removed by filtration and the remaining product purified by chromatography on silica gel (eluant: ethyl acetate/hexane=2/1) to give 2,3-dimethyl-2,3-dihydro-thieno[3,4-b][1,4]dioxine-5,7-dicarboxylic acid diethyl ester as white crystals in 1.5 g (60%) with a melting point of 105° C.; $^1$HNMR (300 MHz, CDCl$_3$) δ 4.45 (q, J=6.6 Hz, 2H), 4.32 (q, J=7.1 Hz, 4H), 1.38 (d, J=7.0 Hz, 6H), 1.37 (t, J=7.1 Hz, 6H); HRMS (FAB) calcd for $C_{14}H_{18}O_6S$ (MH$^+$) 315.0902, found 315.0902; Analysis: Calculated for $C_{14}H_{18}O_6S$: C, 53.49; H, 5.77; S, 10.20. Found: C, 53.43; H, 5.72; S, 10.22.

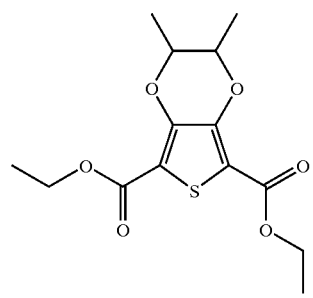

This diethyl ester could be hydrolyzed and decarboxylated following the procedures described by Kumar et al. in 1998 in Chemistry of Materials, volume 10, pages 896–902, to yield pure 2,3-dimethyl-2,3-dihydro-thieno[3,4-b][1,4]dioxine in excellent yield.

INVENTION EXAMPLE 4

Synthesis of 2,3-Dimethyl-2,3-dihydro-thieno[3,4-b][1,4]dioxine-5,7-dicarboxylic Acid Diethyl Ester via the Mitsunobu Reactior ADC01 (2.9 g, 16.9 mmol) was slowly added to a solution of 3,4-dihydroxythiophene-2,5-dicarboxylate acid diethyl ester (2.0 g, 7.7 mmol), meso-2,3-butanediol (0.77 g, 8.5 mmol), and PH02 (4.4 g, 16.9 mmol) in dry tetrahydrofuran (150 ml) at 25° C. The reaction mixture was stirred for 3 h and then refluxed for 2 days. The reaction mixture was allowed to cool to 25° C. and concentrated by rotary evaporator to remove the tetrahydrofuran. The residue was diluted with diethyl ether allowed to stand overnight to enable the triphenylphosphine oxide to precipitate out. The triphenylphosphine oxide was then removed by filtration and the remaining product purified by chromatography on silica gel (eluant: ethyl acetate/hexane=2/1) to give 2,3-dimethyl-2,3-dihydro-thieno[3,4-b][1,4]dioxine-5,7-dicarboxylic acid diethyl ester as white crystals in 0.6–0.75 g (25–30%) yield as characterized by H NMR, $^{13}$C NMR, HRMS, and elemental analysis.

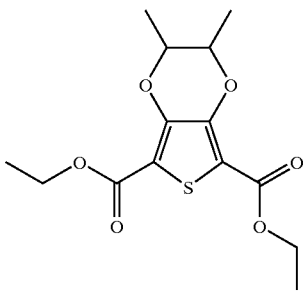

This diethyl ester could be hydrolyzed and decarboxylated following the procedures described by Kumar et al. in 1998 in Chemistry of Materials, volume 10, pages 896–902, to yield pure 2,3-dimethyl-2,3-dihydro-thieno[3,4-b][1,4]dioxine in excellent yield.

INVENTION EXAMPLE 5

Synthesis of 3,3-Diethyl-3,4-dihydro-2H-thieno[3,4-b][1,4]dioxepine-6,8-dicarboxylic Acid Diethyl Ester via the Mitsunobu Reaction ADC01 (2.9 g, 16.9 mmol) was slowly added to a solution of 3,4-dihydroxythiophene-2,5-dicarboxylate acid diethyl ester (2.0 g, 7.7 mmol), 2,2-diethyl-1,3-propanediol (1.1 g, 8.5 mmol), and PH01(3.4 g, 16.9 mmol) in dry tetrahydrofuran (150 ml) at 25° C. The reaction mixture was stirred for 3 h and then refluxed for 21 h. The reaction mixture was allowed to cool to 25° C. and then concentrated by rotary evaporator to remove the tetrahydrofuran. The residue was diluted with diethyl ether and allowed to stand overnight to enable the tributylphosphine oxide to precipitate out. The tributylphosphine oxide was then removed by filtration and the residue purified by chromatography on silica gel (eluant: ethyl acetate/hexane=2/1) to give 3,3-diethyl-3,4-dihydro-2H-thieno[3,4-b][1,4]dioxepine-6,8-dicarboxylic acid diethyl ester as a white solid [yield=2.2 g (80%)]; melting point 100° C.; $^1$HNMR (300 MHz, CDCl$_3$) δ 4.20 (q, J=7.1 Hz, 4H), 4.15 (s, 4H), 1.42 (q, J=7.5 Hz, 4H), 1.35 (t, J=7.1 Hz, 6H), 0.85 (t, J=7.5 Hz, 6H); HRMS (FAB) calcd for C$_{17}$H$_{24}$O$_6$S (MH$^+$) 357.1372, found 357.1372; Analysis: Calculated for C$_{17}$H$_{24}$O$_6$S: C, 57.28; H, 6.79; S, 9.00. Found: C, 57.20; H, 6.78; S, 9.02.

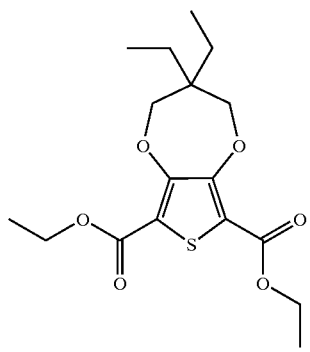

This diethyl ester could be hydrolyzed and decarboxylated following the procedures described by Kumar et al. in 1998 in Chemistry of Materials in 1998, volume 10, pages 896–902, e.g. treatment with 3M sodium hydroxide at 70° C. for 6 h followed by acidification with hydrochloric acid and then heating in quinoline at 150° C. for 12 h in the presence of copper chromite as catalyst; yielding pure 3,3-diethyl-3,4-dihydro-2H-thieno [3,4-b][1,4]dioxepine in excellent yield.

INVENTION EXAMPLE 6

Synthesis of 2-decyl-2,3-dihydro-thieno[3,4-b][1,4]dioxine-5,7-dicarboxylic Acid Diethyl Ester via the Mitsunobu reaction ADC01 (3.22 g, 18.5 mmol) was added slowly to a solution of 3,4-dihydroxythiophene-2,5-dicarboxylate acid diethyl ester (2.0 g, 7.7 mmol), 1,2-dodecanediol (1.88 g, 9.2 mmol) and PH02 (4.84 g, 18.5 mmol) in dry tetrahydrofuran (150 mL) at 25° C. The reaction mixture was stirred for 1 h at 25° C. and then refluxed for 12 h. The reaction mixture was allowed to cool to 25° C. and the tetrahydrofuran was then removed under vacuum. The residue was diluted with diethyl ether and left overnight, whereupon the triphenylphosphine oxide precipitated out. The precipitated triphenylphosphine oxide was then removed by filtration and the residue purified by chromatography on silica gel (ethyl acetate: hexanes=1:3 as eluant) to give 2-decyl-2,3-dihydro-thieno[3,4-b][1,4]dioxine-5,7-dicarboxylic acid diethyl ester as a colourless solid (yield: 2.37 g, 72%); melting point 89–90° C.; $^1$HNMR (300 MHz, CDCl$_3$) δ 4.40 (m, 1H), 4.33 (q, J=7.0 Hz, 4H), 4.29 (m, 1H), 4.03 (dd, J=11.3, 7.6 Hz, 1H), 1.58 (t, J=7.2 Hz, 2H), 1.36 (t, J=6.8 Hz, 6H), 1.23–130 (m, 16H), 0.86 (t, J=6.7 Hz, 4H).

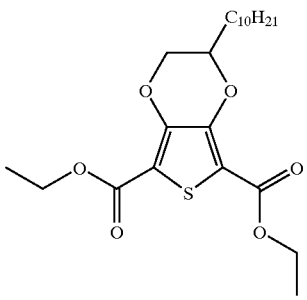

INVENTION EXAMPLE 7

Synthesis of 6-benzyl-2,3-dihydro-6H-[1,4]dioxino[2,3-c]pyrrole-5,7-dicarboxylic acid diethyl ester via the Mitsunobu reaction ADC01 (2.9 g, 16.9 mmol) was slowly added to a solution of N-benzyl-3,4-dihydroxypyrrole-2,5-dicarboxylic acid diethyl ester (2.6 g, 7.7 mmol), ethylene glycol (0.5 g, 8.5 mmol), and PH02 (4.4 g, 16.9 mmol) in dry tetrahydrofuran (150 ml) at 0° C. The reaction mixture was allowed to warm to 25° C., stirred for 3 h, and then was refluxed for 21 h. The reaction mixture was then allowed to cool to 25° C. and was concentrated by rotary evaporator to remove the tetrahydrofuran. The residue was diluted with diethyl ether and allowed to stand overnight to enable the tributylphosphine oxide to precipitate out. The tributylphosphine oxide was then removed by filtration and the residue purified by chromatography on silica gel (eluant: ethyl acetate/hexane=3/1) to give 6-benzyl-2, 3-dihydro-6H-[1,4]dioxino[2,3-c]pyrrole-5,7-dicarboxylic acid diethyl ester as a colourless solid in 2.3 g (85%) yield as characterized by $^1$H NMR, $^{13}$C NMR, HRMS, and elemental analysis.

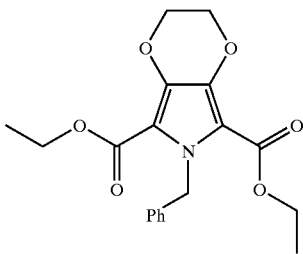

This diethyl ester could be debenzylated, hydrolyzed and decarboxylated as described by Schottland et al. in 2000 in Macromolecules, volume 33, pages 7051–7061, yielding pure 3,4-ethylenedioxypyrrole in excellent yield.

INVENTION EXAMPLE 8

Synthesis of 2-Benzyl-6,6-diethyl-6,7-dihydro-2H, 5H-4,8-dioxa-2-aza-azulene-1,3-dicarboxylic Acid Diethyl Ester via the Mitsunobu Reaction ADC01 (2.9 g, 16.9 mmol) was slowly added to a solution of N-benzyl-3,4-dihydroxypyrrole-2,5-dicarboxylic acid diethyl ester (2.6 g, 7.7 mmol), 2,2-diethyl-1,3-propanediol (1.1 g, 8.5 mmol), and PH02 (4.4 g, 16.9 mmol) in dry tetrahydrofuran (150 ml) at 0° C. The reaction mixture was then allowed to warm to 25° C., stirred for 3 h, and then was refluxed for 21 h. The reaction mixture was then allowed to cool to 25° C. and was concentrated by rotary evaporator to remove the tetrahydrofuran. The residue was then diluted with diethyl ether and allowed to stand overnight to enable the tributylphosphine oxide to precipitate out. The tributylphosphine oxide was then removed by filtration and the remaining product was purified by chromatography on silica gel (eluant: ethyl acetate/hexane=3/1) to give 2-benzyl-6,6-diethyl-6, 7-dihydro-2H,5H-4,8-dioxa-2-aza-azulene-1,3-dicarboxylic acid diethyl ester as a colourless oil in 2.5 g (75%) yield as characterized by $^1$H NMR, $^{13}$C NMR, HRMS, and elemental analysis.

This diethyl ester could be debenzylated, hydrolyzed and decarboxylated as described by Schottland et al. in 2000 in Macromolecules, volume 33, pages 7051–7061, yielding pure 6,6-diethyl-6,7-dihydro-2H,5H-4,8-dioxa-2-aza-azulene in excellent yield.

INVENTION EXAMPLES 9 to 18

Preparation of 3,4-alkylenedioxythiophens

The 3,4-alkylenedioxythiophene derivatives of INVENTION EXAMPLE 9 to 18, P01 to P09, are given in Table 1.

TABLE 1

| Invention Example nr | Product | Structure |
|---|---|---|
| 9 & 10 | P01 | 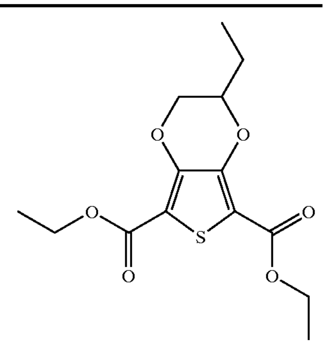 |
| 11 | P02 | 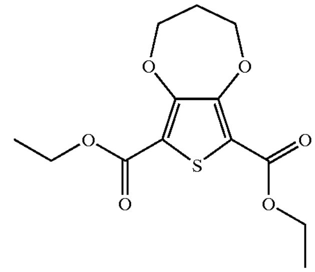 |

TABLE 1-continued

| Invention Example nr | Product | Structure |
|---|---|---|
| 12 | P03 | (3,3-diethyl-propylenedioxy thiophene-2,5-dicarboxylic acid diethyl ester) |
| 13 | P04 | (3,5-dimethyl-propylenedioxy thiophene-2,5-dicarboxylic acid diethyl ester) |
| 14 | P05 | (3,3-dibutyl-propylenedioxy thiophene-2,5-dicarboxylic acid diethyl ester) |
| 15 | P06 | (butylenedioxy thiophene-2,5-dicarboxylic acid diethyl ester) |
| 16 | P07 | (3,3-dimethyl-propylenedioxy thiophene-2,5-dicarboxylic acid diethyl ester) |
| 17 | P08 | (3,3-dimethyl-propylenedioxy thiophene-2,5-dicarboxylic acid di-n-butyl ester) |
| 18 | P09 | (3,3-bis(bromomethyl)-propylenedioxy thiophene-2,5-dicarboxylic acid di-n-butyl ester) |

P01 to P09 were prepared using equimolar quantities of ADC01 and phosphine. ADC01 was added slowly in equimolar quantities with respect to the phosphine used to a solution of 3, 4-dihydroxy-5 thiophene-2,5-dicarboxylic acid diethyl ester [diethyl diester diol] (for quantity see Table 2) or 3,4-dihydroxythiophene-2, 5-dicarboxylic acid di-n-butyl ester [dibutyl diester diol] (for quantity see Table 3), diol (for type and quantity see Tables 2 and 3), and phosphine (for type and quantity see Tables 2 and 3) in dry tetrahydrofuran (150 ml) at 25° C. The reaction mixture was stirred for 3 h and then refluxed (at 66° C.) for the times given in Tables 2 and 3. The reaction mixture was allowed to cool to 25°C. and concentrated by rotary evaporator to remove the THF. The residue was diluted with diethyl ether and allowed to stand overnight to enable the tributylphosphine oxide or triphenylphosphine oxide to precipitate out. The phosphine oxide was then removed by filtration and the residue purified by chromatography on silica gel to give products P01 to P09 (see structures in Table 1) in the yields given in Tables 2 and 3. This diethyl ester could be hydrolyzed and decarboxylated following the procedures described by Kumar et al. in 1998 in Chemistry of Materials, volume 10, pages 896–902, to yield the pure 3,4-alkylenedioxythiophene derivative in the yields given in Tables 2 and 3.

TABLE 2

| Invention Example nr. | diol type | wt. [g] | wt. of diethyl diester diol [g] | phosphine type | wt. [g] | molar ratio of phosphine to diethyl diester diol | Reflux time [h] | Product nr | yield [%] |
|---|---|---|---|---|---|---|---|---|---|
| 9  | 1,2-butanediol | 0.7 | 2.0 | PH01 | 3.0 | 2.0 | 9 | P01 | 70 |
| 10 | 1,2-butanediol | 0.7 | 2.0 | PH02 | 3.9 | 2.0 | 9 | P01 | 70 |
| 11 | 1,3-propanediol | 0.6 | 2.0 | PH01 | 3.0 | 2.0 | 3 | P02 | 92 |
| 12 | 2,2-diethyl-1,3-propanediol | 1.0 | 2.0 | PH01 | 3.0 | 2.0 | 9 | P03 | 85 |
| 13 | 2,4-pentanediol | 0.8 | 2.0 | PH01 | 3.0 | 2.0 | 9 | P04 | 60 |
| 14 | 2,2-dibutyl-1,3-propanediol | 8.7 | 10.0 | PH02 | 24.2 | 2.4 | 9 | P05 | 78 |
| 15 | 1,4-butanediol | 2.3 | 5.5 | PH02 | 13.3 | 2.4 | 9 | P06 | 30 |
| 16 | 2,2-dimethyl-1,3-propanediol | 1.4 | 3.0 | PH02 | 7.3 | 2.4 | 9 | P07 | 74 |

TABLE 3

| Invention Example nr. | diol type | wt. [g] | wt. of dibutyl diester diol [g] | phosphine type | wt. [g] | molar ratio of phosphine to dibutyl diester diol | Reflux time [h] | Product nr | yield [%] |
|---|---|---|---|---|---|---|---|---|---|
| 17 | 2,2-dimethyl-1,3-propanediol | 0.8 | 2.0 | PH02 | 4.0 | 2.4 | 9 | P08 | 95 |
| 18 | 2,2-bis(bromomethyl)-1,3-propanediol | 9.9 | 10.0 | PH02 | 19.9 | 2.4 | 9 | P09 | 79 |

All compounds were fully characterized by $^1$H NMR, $^{13}$C NMR, HRMS, and elemental analysis.

P01 is a colourless solid with a melting point of 130° C.; $^1$HNMR (300 MHz, CDCl$_3$) δ 4.58 (dd, J=12.0, 2.0 Hz, 1H), 4.53 (q, J=7.0 Hz, 4H, 4.38 (m, 1H), 4.23 (dd, J=12.0, 7.6 Hz, 1H), 2.10–1.85 (m, 2H), 1.55 (t, J=7.0 Hz, 3H), 1.54 (t, J=7.0 Hz, 3H), 1.31 (t, J=Hz, 3H); HRMS (FAB) calcd for C$_{14}$H$_{18}$O$_6$S (MH$^+$) 315.0902, found 315,0902; Analysis: Calculated for C$_{14}$H$_{18}$O$_6$S: C, 53.49; H, 5.77; S, 10.20. Found: C, 53.53; H, 5.80; S, 10.21.

P04 is a colorless thick oil; $^1$HNMR (300 MHz, CDCl$_3$) δ 4.70–4.50 (m, 1H), 4.41–4.21 (m, 4H), 4.22–4.12 (m, 1H), 2.22–1.95 (m, 2H), 1.46 9d, J=6.3 Hz, 3H), 1.43 (d, J=6.3 Hz, 3H), 1.34 (t, J=7.1 Hz, 3H), 1.33 (t, J=7.1 Hz, 3H); HRMS (FAB) calculated for C$_{15}$H$_{20}$O$_6$S (MH$^+$) 329.1059, found 329.1059; Analysis: Calculated for C$_{15}$H$_{20}$O$_6$S: C, 54.86; H, 6.14; S, 9.76. Found: C, 54.80; H, 6.17; S, 9.80.

INVENTION EXAMPLES 19 to 23

Preparation of N-benzylated 3,4-alkylenedioxypyrroles

The N-benzylated 3,4-alkylenedioxypyrrole derivatives of INVENTION EXAMPLES 19 to 23, P10 to P14 respectively, are given in Table 4.

TABLE 4

| Invention Example nr | Product | Structure |
|---|---|---|
| 19 | P10 | 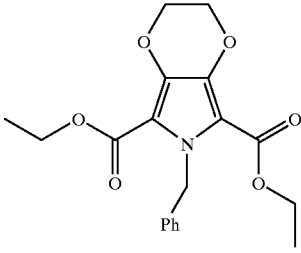 |
| 20 | P11 | 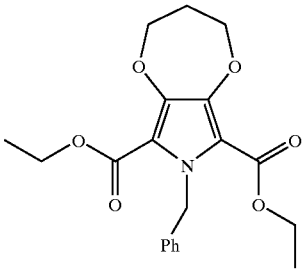 |
| 21 | P12 | 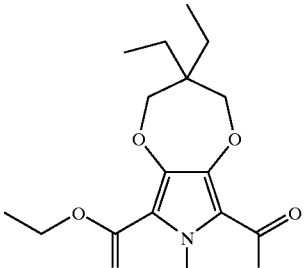 |

TABLE 4-continued

| Invention Example nr | Product | Structure |
|---|---|---|
| 22 | P13 | (structure with Bu, Bu substituents, dioxepine fused pyrrole with diethyl dicarboxylate and N-CH2Ph) |
| 23 | P14 | (structure with dimethyl substituents, dioxepine fused pyrrole with diethyl dicarboxylate and N-CH2Ph) |

P10 to P14 were prepared using equimolar quantities of ADC01 and phosphine. ADC01 was added slowly in equimolar quantities with respect to the phosphine used to a solution of N-benzylated 3, 4-dihydroxypyrrole-2,5-dicarboxylic acid diethyl ester [diethyl diester diol] (for quantity see Table 5), diol (for type and quantity see Table 5), and phosphine (for type and quantity see Table 5) in dry tetrahydrofuran (150 ml) at 25° C. The reaction mixture was stirred for 3 h and then refluxed (at 66° C.) for the time given in Table 5. The reaction mixture was allowed to cool to 25° C. and concentrated by rotary evaporator to remove the THF. The residue was diluted with diethyl ether and allowed to stand overnight to enable the tributylphosphine oxide or triphenylphosphine oxide to precipitate out. The phosphine oxide was then removed by filtration and the residue purified by chromatography on silica gel to give products P10 to P14 (see structures in Table 4) in the yields given in Table 5. These diethl esters could be hydrolyzed and decarboxylated following the procedures described by Kumar et al. in 1998 in Chemistry of Materials, volume 10, pages 896–902, to yield the pure N-benzylated 3,4-alkylenedioxythiophene derivatives in the yields given in Table 5:

All compounds were fully characterized by $^1$H NMR, $^{13}$C NMR, HRMS, and elemental analysis.

The present invention may include any feature or combination of features disclosed herein either implicitly or explicitly or any generalisation thereof irrespective of whether it relates to the presently claimed invention. In view of the foregoing description it will be evident to a person skilled in the art that various modifications may be made within the scope of the invention.

We claim:

1. A process for preparing a heteroaromatic compound having a heteroaromatic nucleus substituted with one or more ether groups comprising the step of: condensing at least one hydroxy-group of a compound having said heteroaromatic nucleus, said at least one hydroxy group (—OH) being substituted at α- or β-positions with respect to a heteroatom of said heteroaromatic nucleus, with an alcohol containing one or more primary or secondary alcohol groups, optionally substituted with nitro, amide, ester, halogen, cyano or (hetero)aromatic groups, using the redox couple of a triaryl- or trialkylphosphine and an azodioxo-compound at a temperature between −40° C. and 160° C.

2. Process according to claim 1, wherein said compound has at least two hydroxy groups substituted at α- or β-positions with respect to a heteroatom of said heteroaromatic nucleus.

3. Process according to claim 1, wherein said heteroaromatic nucleus is selected from the group consisting of pyridine, thiazole, isoxazole, imidazole, pyrazole, 1,2,3-triazole, furan, thiophene, selenophene, pyrrole, pyrazine, pyridazine and pyrimidine.

4. Process according to claim 1, wherein said heteroaromatic nucleus of said compound is further substituted with a nitro, ester, cyano, acyl, acyloxy, carbonato, alkyl, aryl, carbocyclic or heterocyclic group.

5. Process according to claim 1, wherein said heteroaromatic nucleus is annulated to a carbocyclic or a heterocyclic ring system.

6. Process according to claim 5, wherein said annulated heteroaromatic nucleus is selected from the group consisting of indole, isoindole, thianaphthene, benzimidazole, benzofuran, thiophthene, quinoline, isoquinoline, cinnoline and quinoxaline.

7. Process according to claim 1, wherein said alcohol is an optionally substituted diol represented by formula (I):

TABLE 5

| Invention Example nr. | diol type | wt. [g] | wt. of diethyl diester diol [g] | phosphine type | wt. [g] | molar ratio of phosphine to diethyl diester diol | Reflux time [h] | Product nr | yield [%] |
|---|---|---|---|---|---|---|---|---|---|
| 19 | 1,2-ethanediol | 0.6 | 2.5 | PH02 | 4.7 | 2.4 | 45 | P10 | 95 |
| 20 | 1,3-propanediol | 0.7 | 2.5 | PH02 | 4.7 | 2.4 | 45 | P11 | 85 |
| 21 | 2,2-diethyl-1,3-propanediol | 1.2 | 2.5 | PH02 | 4.7 | 2.4 | 45 | P12 | 75 |
| 22 | 2,2-di-n-butyl-1,3-propanediol | 1.7 | 2.5 | PH02 | 4.7 | 2.4 | 45 | P13 | 60 |
| 23 | 2,2-dimethyl-1,3-propanediol | 1.0 | 2.5 | PH02 | 4.7 | 2.4 | 45 | P14 | 80 |

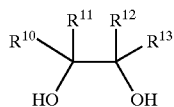

(I)

wherein $R^{10}$, $R^{11}$, $R^{12}$ and $R^{13}$ independently represent hydrogen or alkyl, alkoxy or aryl groups optionally substituted with nitro, amide, ester, halogen, cyano or (hetero)aromatic groups.

8. Process according to claim 1, wherein said alcohol is an optionally substituted diol represented by formula (II):

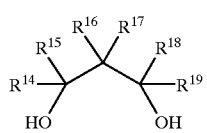

(II)

where $R^{14}$, $R^{15}$, $R^{16}$, $R^{17}$ $R^{18}$ and $R^{19}$ independently represent hydrogen or alkyl, alkoxy or acyl groups optionally substituted with nitro, amide, ester, halogen, cyano or (hetero)aromatic groups.

9. Process according to claim 1, wherein said heteroaromatic compound is a 3,4-ethylenedioxythiophene or a 3,4-ethylenedioxypyrrole represented by formula (V):

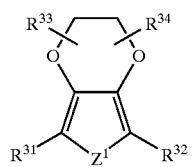

(V)

wherein $R^{31}$ and $R^{32}$ independently represent optionally substituted alkyl, alkoxy, carboxy or cycloalkyl substituents, $R^{33}$ and $R^{34}$ independently represent unsaturated or saturated substituents such as alkyl or alkoxy groups optionally substituted with nitro, amide, ester, halogen, cyano or (hetero)aromatic groups, and $Z^1$ is S or N—$R^{35}$ where $R^{35}$ is an optionally substituted acyl or alkyl group.

10. Process according to claim 1, wherein said heteroaromatic compound is a 3,4-propylenedioxythiophene or a 3,4-propylenedioxypyrrole represented by formula (VI):

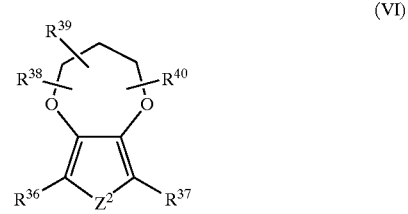

(VI)

wherein $R^{36}$ and $R^{37}$ independently represent optionally substituted alkyl, alkoxy, carboxy or cycloalkyl substituents, $R^{38}$, $R^{39}$ and $R^{40}$ independently represent unsaturated or saturated substituents such as alkyl or alkoxy groups optionally substituted with nitro, amide, ester, halogen, cyano or (hetero)aromatic groups, and $Z^2$ is S or N—$R^{41}$ where $R^{41}$ is an optionally substituted acyl or alkyl group.

* * * * *